(12) United States Patent
Allen et al.

(10) Patent No.: US 9,082,201 B2
(45) Date of Patent: Jul. 14, 2015

(54) SURFACE CONTAMINATION DETERMINATION SYSTEM

(71) Applicant: International Business Machines Corporation, Armonk, NY (US)

(72) Inventors: Ira L. Allen, Dallas, TX (US); Rogerio S. Feris, Hartford, CT (US); Yun Zhai, Bedford Hills, NY (US)

(73) Assignee: International Business Machines Corporation, Armonk, NY (US)

( * ) Notice: Subject to any disclaimer, the term of this patent is extended or adjusted under 35 U.S.C. 154(b) by 261 days.

(21) Appl. No.: 13/734,746

(22) Filed: Jan. 4, 2013

(65) Prior Publication Data

US 2014/0193042 A1 Jul. 10, 2014

(51) Int. Cl.
*G06K 9/00* (2006.01)
*G06T 7/40* (2006.01)
*G06T 7/00* (2006.01)

(52) U.S. Cl.
CPC ............... *G06T 7/408* (2013.01); *G06T 7/0004* (2013.01); *G06T 2207/10024* (2013.01); *G06T 2207/30156* (2013.01)

(58) Field of Classification Search
None
See application file for complete search history.

(56) References Cited

U.S. PATENT DOCUMENTS

| | | | |
|---|---|---|---|
| 4,943,734 A | 7/1990 | Johnson et al. | |
| 5,426,506 A | 6/1995 | Ellingson et al. | |
| 5,654,799 A | 8/1997 | Chase et al. | |
| 5,748,299 A | 5/1998 | Esmaeili | |
| 7,652,584 B2 | 1/2010 | Fridthjof | |
| 2005/0279385 A1 | 12/2005 | Grier et al. | |
| 2007/0227558 A1 | 10/2007 | Chase | |
| 2008/0127436 A1 | 6/2008 | MacDowell | |
| 2008/0300724 A1 | 12/2008 | De Silvio et al. | |
| 2010/0328476 A1* | 12/2010 | Wagner | 348/222.1 |

FOREIGN PATENT DOCUMENTS

| | | |
|---|---|---|
| JP | 2011173553 A | 9/2011 |
| JP | 2012001073 A | 1/2012 |
| WO | 2008110175 A1 | 9/2008 |

OTHER PUBLICATIONS

"The professional line of car washing plants". Gantry Car Washes. K'A'RCHER CWP 2000. Germany.
"High Performance Efficient Wash!", LaserWash® Touch Free G5 S-Series, Vehicle Wash Systems, PDQ Manufacturing Inc., De Pere, WI, USA, Feb. 2008, 4 pages.

* cited by examiner

*Primary Examiner* — Nirav G Patel
(74) *Attorney, Agent, or Firm* — Jinesh Patel; Matthew Chung

(57) ABSTRACT

A computer receives a first set of spectral information for a first surface, wherein the first set of spectral information includes a pixel count for each color value of a range of color values, with regard to each color, measured at time one. The computer determines, with regard to the first set, whether dispersion of the pixel count across the range of color values, with regard to each color, exceeds a first threshold value. The computer determines, with regard to the first set, a surface contamination level based on at least whether the dispersion of the pixel count across the range of color values, with regard to each color, exceeds the first threshold value.

18 Claims, 6 Drawing Sheets

SURFACE CONTAMINATION DETERMINATION SYSTEM

FIELD OF THE INVENTION

The present invention relates generally to the reflection and refraction of light, and more particularly to detecting the level of contaminations on a surface by analyzing light reflection and refraction.

BACKGROUND

Dirt detection is important for many different applications such as systems with the objective to restore cleanliness; an example is automatic car wash systems. For automatic car wash systems, several factors play in to cleaning the surface of a vehicle such as the type, size and the amount of dirt present on the surface of a vehicle. Currently, automatic car wash systems, such as roll over wash systems, include a moving gantry equipped with wash equipment that travels on tracks on a floor or building walls and moves about a stationary vehicle applying soaps, cleaners, waxes and rinses. Other automatic car wash systems, such as tunnel or conveyor washes, use push or pull equipment to move a vehicle through wash equipment disposed within the tunnel. Positioning the vehicle and appropriately allocating cleaning resources, such as soap and water, to the different areas of the vehicle is paramount to delivering the cleanest vehicle possible back to the consumer.

SUMMARY

Embodiments of the present invention provide a system, method, and program product for determining a surface contamination level for a first surface. A computer receives a first set of spectral information for a first surface, wherein the first set of spectral information includes a pixel count for each color value of a range of color values, with regard to each color, measured at time one. The computer determines, with regard to the first set, whether dispersion of the pixel count across the range of color values, with regard to each color, exceeds a first threshold value. The computer determines, with regard to the first set, a surface contamination level based on at least whether the dispersion of the pixel count across the range of color values, with regard to each color, exceeds the first threshold value.

DETAILED DESCRIPTION

Figure 1:
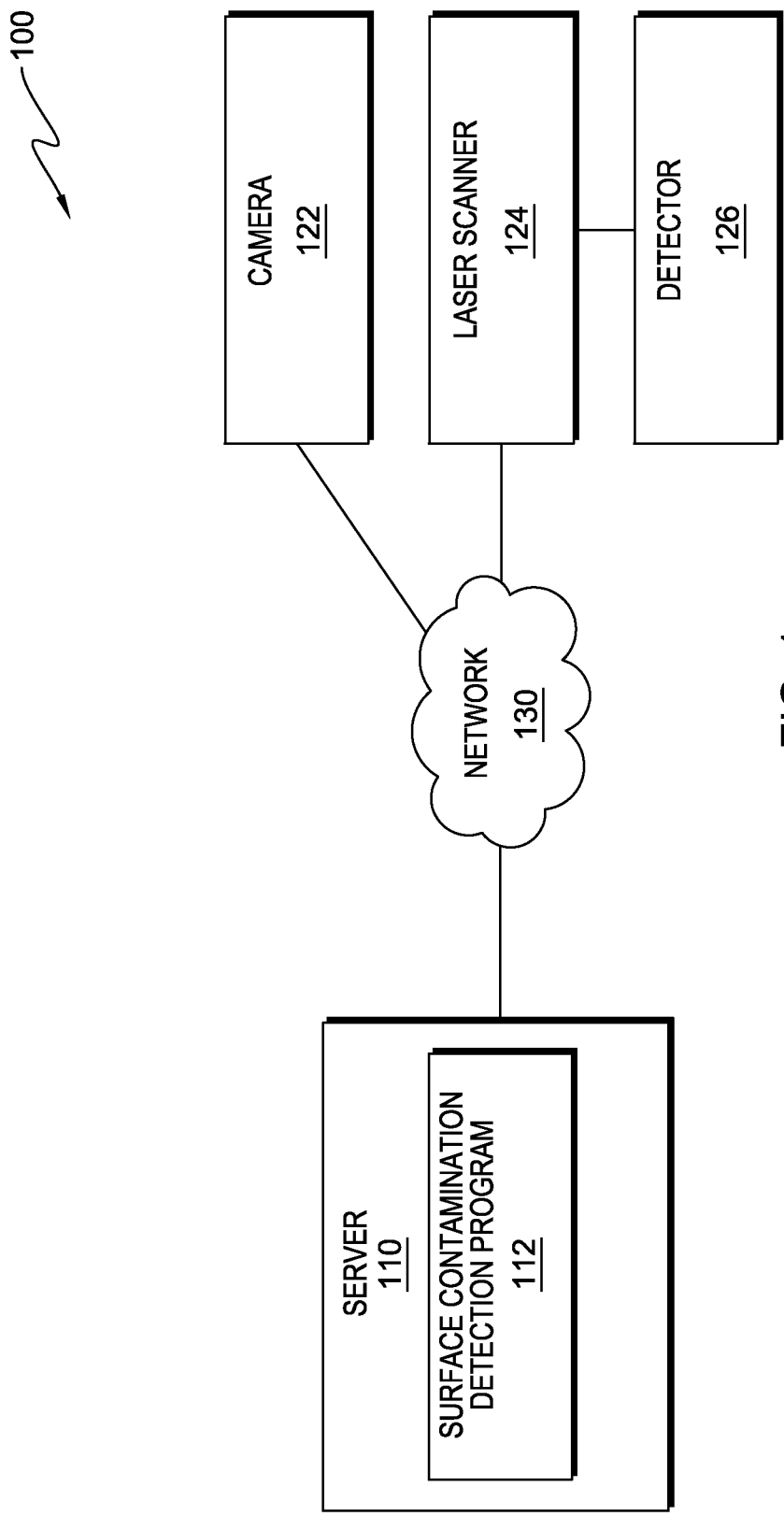
FIG. 1 illustrates a surface contamination detection system, in accordance with an embodiment of the invention.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer-readable medium(s) having computer-readable program code/instructions embodied thereon.

Any combination of one or more computer-readable medium(s) may be utilized. The computer-readable medium may be a computer-readable signal medium or a computer-readable storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain, or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device.

Program code embodied on a computer-readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer, other programmable data processing apparatus, or other devices to function in a particular manner, such that the instructions stored in the computer-readable medium produce an article of manufacture including instructions, which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices, to produce a computer-implemented process such that the instructions which execute on the computer or other programmable apparatus provide processes for implementing the functions/acts specified in the flowchart and/or block diagram block or blocks.

Embodiments of the present invention will now be described in detail with reference to the accompanying Figures.

FIG. 1 illustrates surface contamination detection system 100, in accordance with an embodiment of the invention. Surface contamination detection system 100 includes server 110, camera 122 and laser scanner 124, interconnected over network 130.

In an exemplary embodiment, network 130 is the Internet, representing a worldwide collection of networks and gateways to support communications between devices connected to the Internet. In the exemplary embodiment, network 130 is also a collection of networks and gateways capable of communicating global positioning information between devices connected to the network. Network 130 may include, for example, wired, wireless or fiber optic connections. In other embodiments, network 130 may be implemented as an intranet, a local area network (LAN), or a wide area network (WAN). In general, network 130 can be any combination of connections and protocols that will support communications between server 110, camera 122 and laser scanner 124, in accordance with embodiments of the invention. In other embodiments, server 110 may be hard-wired or directly connected to camera 122 and laser scanner 124. In other embodiments, camera 122 and/or laser scanner 124 may be fully or partially integrated components of server 110.

Camera 122 is a hardware device capable of capturing images of an object. In the exemplary embodiment, camera 122 also contains components, such as a network interface card, which allows camera 122 to send and receive information from server 110. Camera 122 also contains components to capture and analyze a beam of light (natural or artificial) reflected or refracted off the surface of an object and measure the color value percentage for a range of brightness values, with regard to each spectral color, of the reflected or refracted beam of light.

Laser scanner 124 is a hardware device capable of projecting a laser beam onto the surface of an object. In the exemplary embodiment, laser scanner 124 also contains components, such as a network interface card, which allows laser 124 to send and receive information from server 110. Laser scanner 124 also contains components to capture and analyze a laser beam or beam of light that has reflected or refracted off the surface of an object and measure the pixel count for a range of color values, with regard to each spectral color, of the laser beam or beam of light. In the exemplary embodiment, the size of dispersal of the reflected/refracted laser beam is measured, which serves as an indication of the level of contamination present on the surface.

Server 110 includes surface contamination detection program 112. Server 110 may be a desktop computer, a notebook, a laptop computer, a tablet computer, a handheld device, a smart-phone, a thin client, or any other electronic device or computing system capable of receiving and sending data to and from camera 122 and laser scanner 124 via network 130. Server 110 is described in more detail with reference to FIG. 4.

In the exemplary embodiment, surface contamination detection program 112 includes components to analyze images and light reflection/refraction data, such as pixel counts for a range of color values of a spectral color, received from camera 122 and laser scanner 124 via network 130, and determine a surface contamination level of a surface. The operation of surface contamination detection program 112 is described in further detail below with reference to FIGS. 2 and 3.

The foregoing description of various embodiments of the present invention has been presented for purposes of illustration and description. It is not intended to be exhaustive nor to limit the invention to the precise form disclosed. Many modifications and variations are possible. Such modifications and variations that may be apparent to a person skilled in the art of the invention are intended to be included within the scope of the invention as defined by the accompanying claims.

Figure 2:
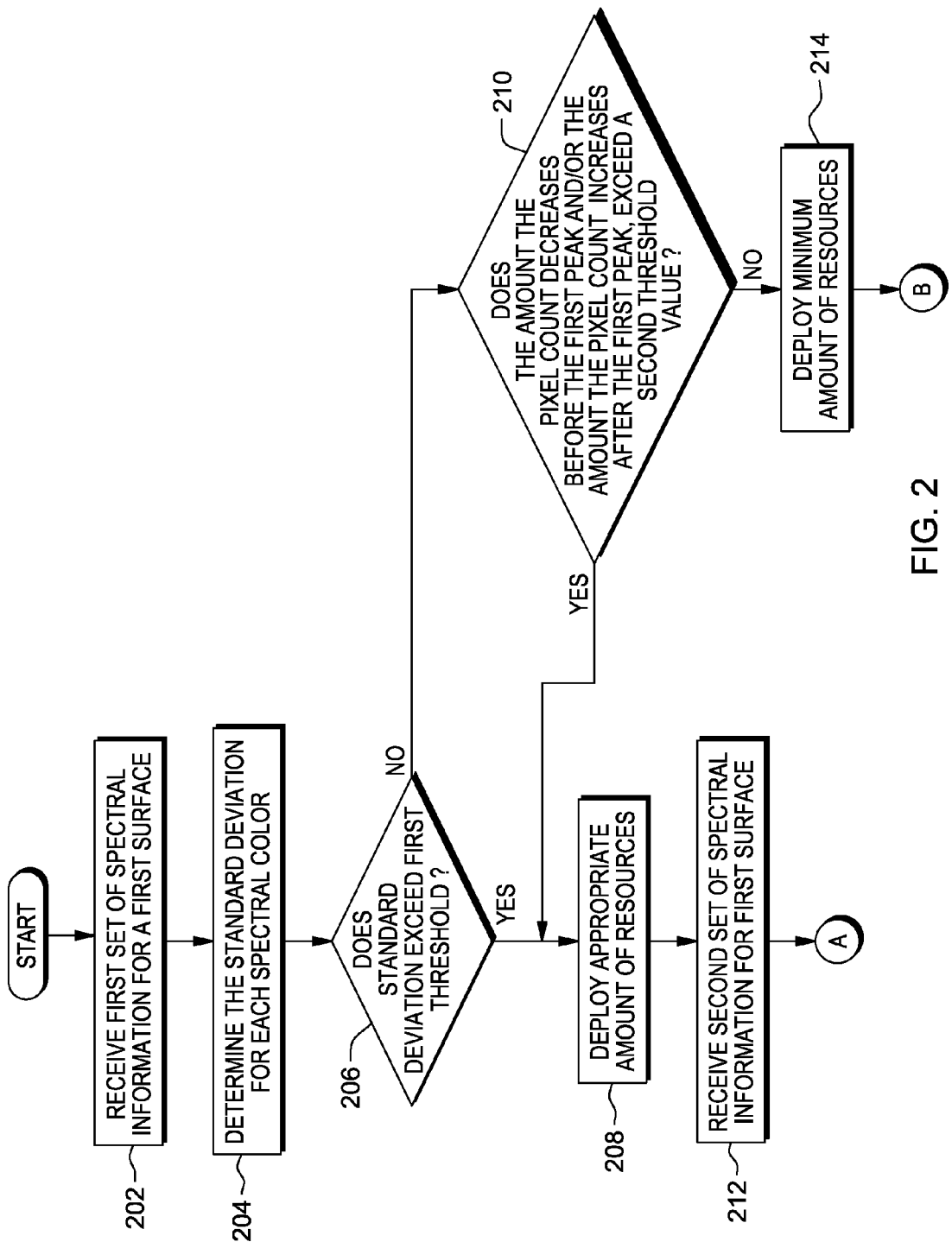
FIGS. 2 and 3 depict a flowchart illustrating the operations of the surface contamination detection program of FIG. 1 in detecting the level of dirt on a surface and allocating the appropriate cleaning resources, in accordance with an embodiment of the invention.
Figure 3:
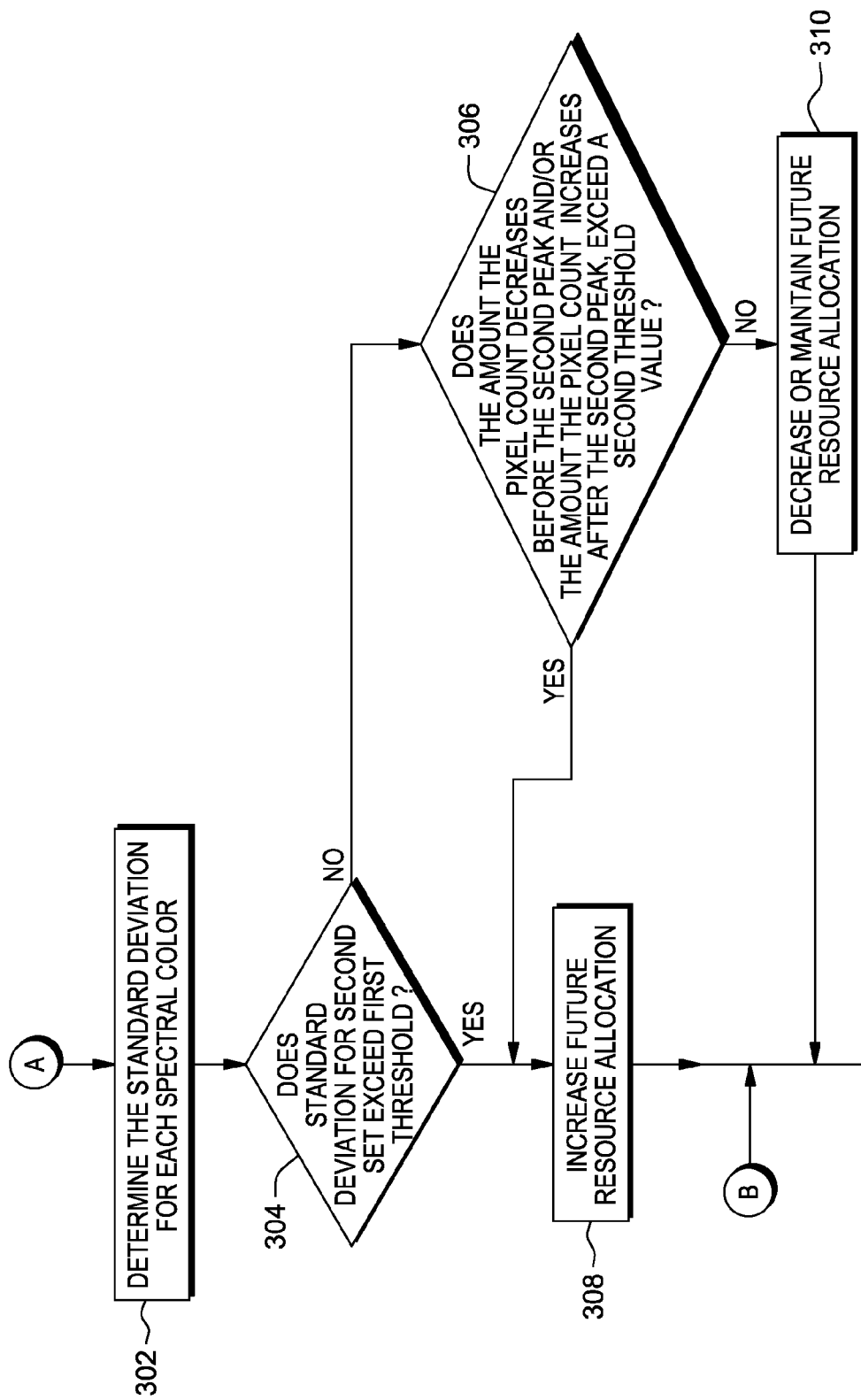

FIGS. 2 and 3 depict a flowchart illustrating the operations of surface contamination detection program 112 in detecting the surface contamination level on a first surface and allocating the appropriate cleaning resources, in accordance with an embodiment of the invention. In the exemplary embodiment, surface contamination detection program 112 receives a first set of spectral information for a first surface from camera 122 and/or laser scanner 124 via network 130 (step 202). In the exemplary embodiment, surface contamination detection program 122 can retrieve spectral information from either camera 122 or laser scanner 124 or both. It is up to the discretion of the user to determine whether to analyze one or both sets of spectral information. In the exemplary embodiment, camera 122 collects spectral information of the natural or artificial light reflecting or refracting off the first surface. Laser scanner 124 can be used in a more precise manner. Laser scanner 124 shines one or more laser beams onto the first surface and collects spectral information for the beam(s) that reflects or refracts off the first surface. In essence, because laser scanner 124 can focus a laser beam on a small area, laser scanner 124 can provide a precise measurement of spectral information for a small area, if a user desires to analyze the surface contamination level of a small area. In the exemplary embodiment, spectral information includes a pixel count for each color value within a range of color values, with regard to each spectral color. For example, with regard to the spectral color blue, camera 122 and/or laser scanner 124 measure the amount of each shade of blue, each shade denoted by a specific color value, present in a reflected or refracted beam of light. A color value for a color is expressed by a number ranging from 0 to 255, with 0 representing the darkest shade of the color and 255 representing the lightest shade of the color. Therefore, in the exemplary embodiment, surface contamination detection program 112 receives a pixel count ranging from 0 to 1, for each color value, ranging from 0 to 255, for each spectral color being measured. In the exemplary embodiment, the spectral information measured is limited to the traditional spectral colors of red, orange, yellow, green, blue, and violet. In other embodiments, spectral information for other colors may also be measured and analyzed.

In the exemplary embodiment, with regard to the first set of spectral information, surface contamination detection program 112 determines the standard deviation of the color value, with regard to each spectral color (step 204). In other embodiments, surface contamination detection program 112 may determine variance or another statistical dispersion of the pixel count for the range of color values, with regard to each spectral color. In the exemplary embodiment, the larger the standard deviation value, the higher the level of contamination present on the first surface. This is due to the fact that contaminants present on the a surface cause the pixel count of the light reflected or refracted off the surface to be dispersed across a wider range of color values than light reflected or refracted off a clean surface. The greater the dispersal of the pixel count, the greater the standard deviation, therefore, the resulting standard deviation for a contaminated surface is greater than the resulting standard deviation for a clean surface. In addition, portions of the first set of spectral information may also be analyzed individually. Analyzing specific portions may be useful for surfaces that contain a large amount of contamination.

Surface contamination detection program 112 then determines whether the standard deviation, for at least one color, exceeds a first threshold value (decision 206). In the exemplary embodiment, the first threshold value is 10, which represents the approximate value of the standard deviation of the color value, with regard to a spectral color, for a beam of light reflected or refracted off a clean surface. In other embodiments, the first threshold may be another value. If surface contamination detection program 112 determines that the standard deviation of the color value, for at least one color, exceeds the first threshold value (decision 206, "YES" branch), surface contamination detection program 112 deploys an appropriate amount of resources based on the amount that the determined standard deviation exceeds the first threshold by (step 208). For example, if surface contamination detection program 112 determines that the standard deviation for at least one color exceeds the first threshold value by 15, surface contamination detection program 112 may deploy a large amount of resources so a thorough clean can be performed. However, if surface contamination detection program 112 determines that the standard deviation for at least one color only exceeds the first threshold value by 4; surface contamination detection program 112 may deploy a standard amount of resources. The exact amount of resources deployed is up to the discretion of the user.

If surface contamination detection program 112 determines that the standard deviation of the color value, for at least one color, does not exceed the first threshold value (decision 206, "NO" branch), surface contamination detection program 112 determines whether the amount that the pixel count decreases before the first peak value is reached, or the amount the pixel count increases after the first peak value has been reached, exceeds a second threshold value (decision 210). In the exemplary embodiment, the first peak value is the color value that corresponds to the highest pixel count, with regard to the first set, and the second threshold value is 0.2. In other embodiments, the second threshold value can be another value. When analyzing color value from a graphical viewpoint, the first peak value would be the color value where the peak point of the curve lies. As stated above, contaminants on a surface can cause a dispersion of the color value greater than the dispersion for a clean surface. This can result in small peaks and valleys on either side of the first peak of the curve. For color values less than the peak value, contaminants present on the first surface may cause the corresponding pixel count to decrease abruptly on the way up to the peak value. For color values greater than the peak value, contaminants present on the first surface may cause the corresponding pixel counts to increase abruptly on the way down from the peak value. By determining if there is an abrupt decrease in pixel count before the peak value is reached or an abrupt increase in pixel count after the peak value is reached, surface contamination detection program 112 determines if there are any small peaks and valleys on either side of the first peak.

If surface contamination detection program 112 determines that the amount the pixel count decreases before the first peak and the amount the pixel count increases after the first peak, does not exceed the second threshold value (decision 210, "NO" branch), surface contamination detection program 112 deploys a minimum amount of resources (step 214). A minimum amount of resources are deployed because surface contamination detection program 112 determined that the standard deviation does not exceed a first threshold and that no peak and valleys exist prior to and after the first peak. Therefore, the first surface does not contain a large amount of contaminants and can be cleaned with a minimal amount of cleaning resources.

If surface contamination detection program 112 determines that the amount the pixel count decreases before the first peak or the amount the pixel count increases after the first peak, exceeds the second threshold value (decision 210, "YES" branch), surface contamination detection program 112 deploys an appropriate amount of resources based on the amount that the pixel count increase or decrease exceeds the second threshold by (step 208). For example, if surface contamination detection program 112 determines that the pixel count increase or decrease exceeds the second threshold by 0.2, a larger amount of resources may be deployed than if the pixel count increase or decrease exceeds the second threshold only by 0.05. In addition, in the exemplary embodiment, if surface contamination detection program 112 determines that there are multiple pixel count increases and/or decreases that exceed the second threshold value, surface contamination detection program 112 may deploy an even larger amount of resources. As stated above, the exact amount of resources deployed is up to the discretion of the user.

Surface contamination detection program 112 then receives a second set of spectral information for the first surface from camera 122 and/or laser scanner 124 via network 130 (step 212). In the exemplary embodiment, the second set of spectral information is measured by camera 122 and/or laser scanner 124 at a time after surface contamination detection program 112 deploys an appropriate amount of resources (step 208). In addition, as stated above, in the exemplary embodiment, spectral information includes a pixel count for each color value within a range of color values, with regard to each spectral color.

In the exemplary embodiment, with regard to the second set of spectral information, surface contamination detection program 112 determines the standard deviation of the color value, with regard to each spectral color (step 302). As stated above, in other embodiments, surface contamination detection program 112 may determine variance or another statistical dispersion of the color value, with regard to each spectral color. Since surface contamination detection program 112 has already deployed an appropriate amount of resources to clean the first surface (step 208), the first surface should contain less contaminants than when the first set of spectral information was measured and, therefore, the standard deviation for the second set should be less than the standard deviation for the first set. However, the first surface may still contain some level of contaminants.

To check for leftover contaminants, with regard to the second set, surface contamination detection program 112 determines whether the standard deviation of the color value, with regard to each color, exceeds a first threshold value (decision 304). In the exemplary embodiment, the first threshold value is 10, which represents the approximate value of the standard deviation of the color value, with regard to a spectral color, for a beam of light reflected or refracted off a clean surface. In other embodiments, the first threshold may be another value. If surface contamination detection program 112 determines that the standard deviation of the color value, for at least one color, exceeds the first threshold value (decision 304, "YES" branch), surface contamination detection program 112 increases the amount of resources that will be deployed for future surfaces with the same level of surface contamination (step 308). For example, if surface contamination detection program 112 determines that the standard deviation for the second set exceeds the first threshold value by 8, surface contamination detection program 112 may increase the amount of resources that will be deployed in the future for a surface with a similar surface contamination level as the first surface by a fairly large amount. However, if surface contamination detection program 112 determines that the standard deviation for the second set only exceeds the first threshold value by 1 or 2, surface contamination detection program 112 may only increase the amount of resources to be deployed in the future for a similar surface contamination level as the first surface by a small amount or not at all. The exact amount of the increase in resources is up to the discretion of the user.

If surface contamination detection program 112 determines that the standard deviation of the color value, for at least one color, does not exceed the first threshold value (decision 304, "NO" branch), surface contamination detection program 112 determines whether the amount that the pixel count decreases before the second peak value is reached, or the amount the pixel count increases after the second peak value has been reached, exceeds a second threshold value (decision 306). In the exemplary embodiment, the second peak value is the color value that corresponds to the highest pixel count, with regard to the second set, and the second threshold value is 0.2. As stated above, contaminants on a surface can cause a dispersion of the color value percentages which can result in small peaks and valleys on either side of the second peak value. This serves as a second check for contaminants to fully examine whether the first surface was effectively cleaned by the amount of resources deployed by surface contamination detection program 112.

If surface contamination detection program 112 determines that the amount the pixel count decreases before the second peak value and the amount the pixel count increases after the second peak value, does not exceed the second threshold value (decision 306, "NO" branch), surface contamination detection program 112 maintains or incrementally decreases the amount of resources which will be deployed for future surfaces that have similar levels of surface contamination (step 310). If both the standard deviation of the second set does not exceed the first threshold (step 304), and the amount the pixel count decreases before the second peak value and the amount the pixel count increases after the second peak value, does not exceed the second threshold value, the first surface is clean. It is up to the discretion of the user whether to incrementally decrease the amount of resources deployed in the future for surfaces with a similar level of surface contamination in order to conserve resources or to maintain the amount of resources to be deployed as is.

If surface contamination detection program 112 determines that the amount the pixel count decreases before the second peak value or the amount the pixel count increases after the second peak value, exceeds the second threshold value (decision 306, "YES" branch), surface contamination detection program 112 increases the amount of resources that will be deployed for future surfaces with the same level of surface contamination (step 308). For example, if surface contamination detection program 112 determines that the amount the pixel count decreases before the second peak value or the amount the pixel count increases after the second peak value for the second set exceeds the second threshold value by 0.15, surface contamination detection program 112 may increase the amount of resources that will be deployed in the future for a surface with a similar surface contamination level as the first surface by a fairly large amount. However, if surface contamination detection program 112 determines that the amount the pixel count decreases before the second peak value or the amount the pixel count increases after the second peak value for the second set only exceeds the second threshold value by 0.05, surface contamination detection program 112 may only increase the amount of resources to be deployed in the future for a similar surface contamination level as the first surface by a small amount or not at all. The exact amount of the increase in resources is up to the discretion of the user.

Figure 4:
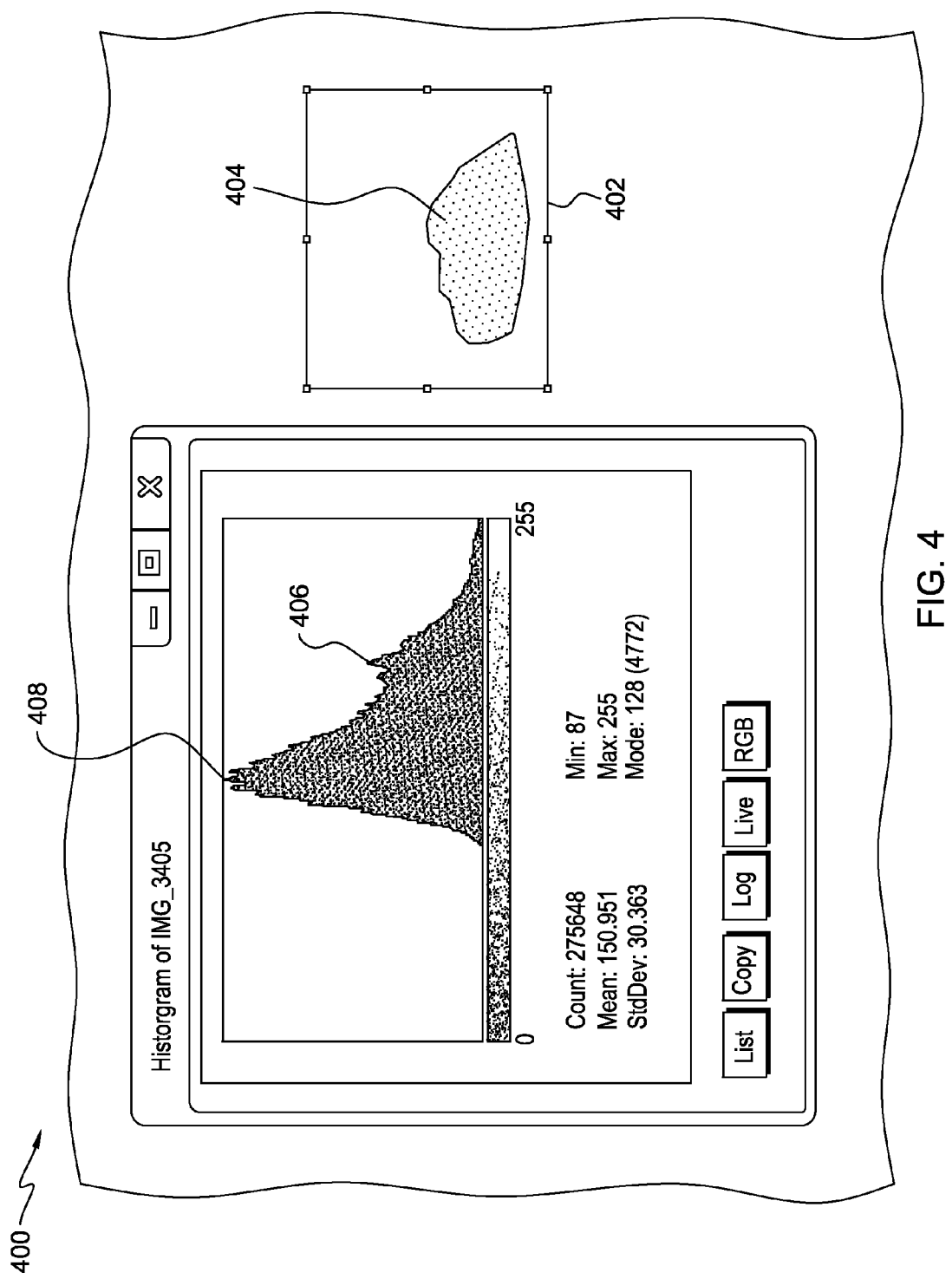
FIG. 4 is a histogram which graphically illustrates spectral information for a contaminated surface, in accordance with an embodiment of the invention.

FIG. 4 depicts histogram 400 which graphically illustrates spectral information for a contaminated surface, in accordance with an exemplary embodiment of the invention. In the exemplary embodiment, the y-axis represents the pixel count and the x-axis represents the color value for a spectral color. As depicted in the figure, area 402, the area being examined, contains contaminant 404. The presence of contaminant 404 is reflected by the dispersion of the pixel count across the range of color values of the histogram. In addition, the presence of contaminant 404 is reflected by small peak 406, which forms after peak value 408 is reached.

Figure 5:
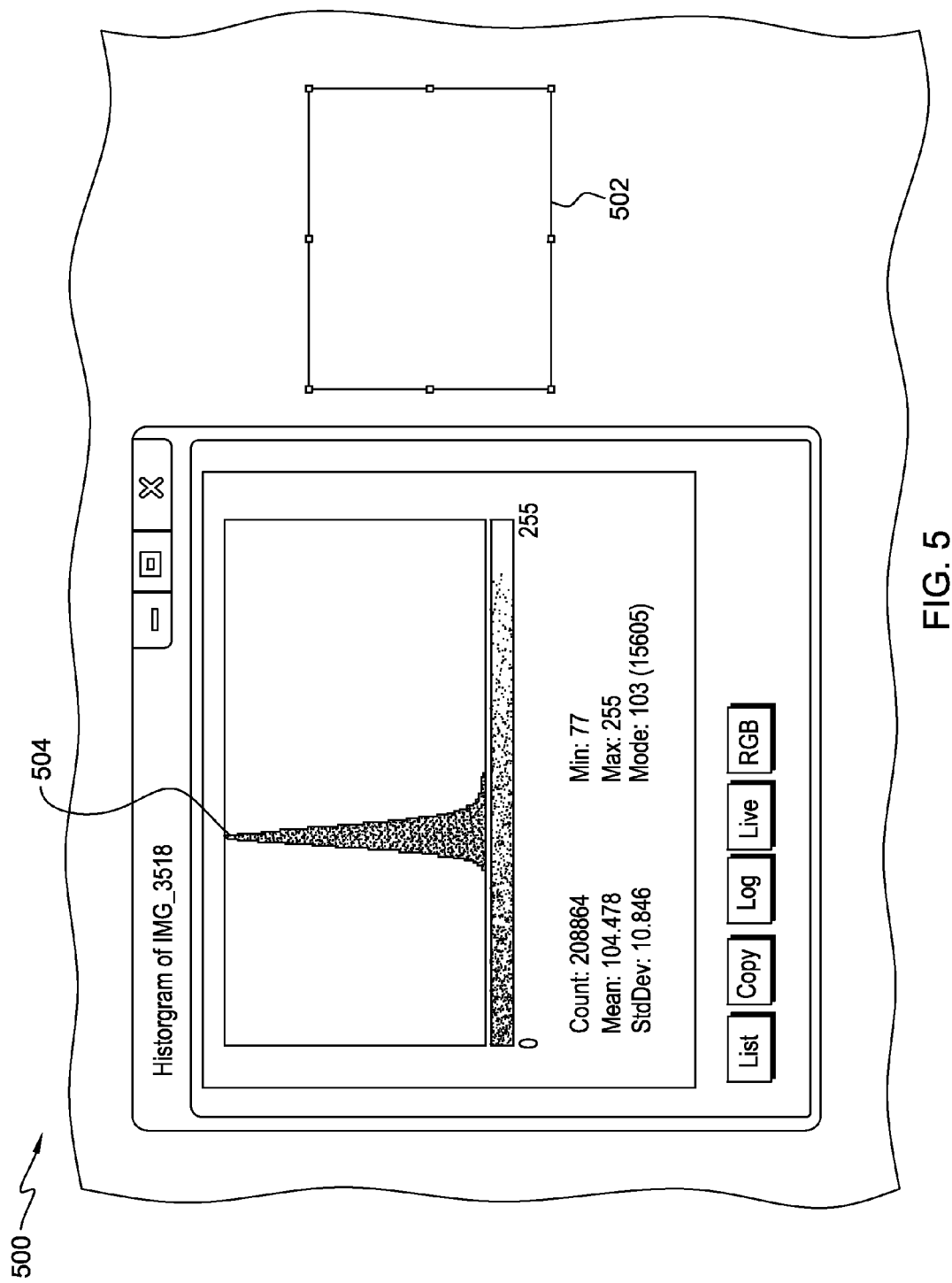
FIG. 5 is a histogram which graphically illustrates spectral information for a clean surface, in accordance with an embodiment of the invention.

FIG. 5 depicts histogram 500 which graphically depicts spectral information for a clean surface, in accordance with an exemplary embodiment of the invention. In the exemplary embodiment, as stated above, the y-axis represents the pixel count and the x-axis represents the color value for a spectral color. As depicted in the figure, area 502, the area being examined, does not contain a contaminant. Area 502 is clean resulting in the dispersion of the pixel count across the range of color values of the histogram to be smaller than the dispersion measured with regard to area 402. In addition, the pixel count increases uniformly up to peak value 504 and then decreases uniformly down from peak value 504, without any small peaks or valleys being present.

Figure 6:
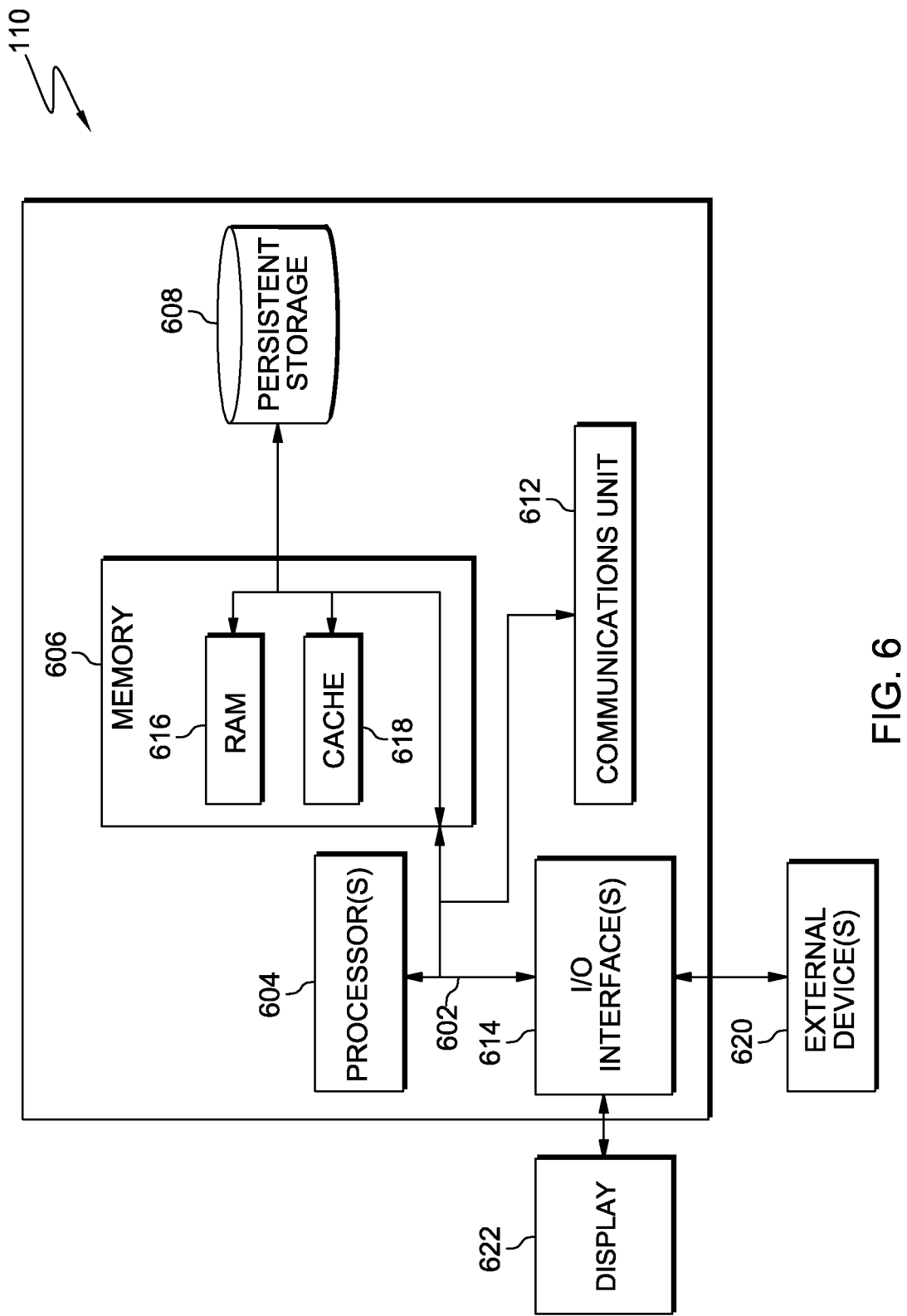
FIG. 6 is a block diagram depicting the hardware components of the surface contamination detection system of FIG. 1, in accordance with an embodiment of the invention

FIG. 6 depicts a block diagram of components of server 110, in accordance with an illustrative embodiment of the present invention. It should be appreciated that FIG. 6 provides only an illustration of one implementation and does not imply any limitations with regard to the environments in which different embodiments may be implemented. Many modifications to the depicted environment may be made.

Server 110 includes communications fabric 602, which provides communications between computer processor(s) 604, memory 606, persistent storage 608, communications unit 612, and input/output (I/O) interface(s) 614. Communications fabric 602 can be implemented with any architecture designed for passing data and/or control information between processors (such as microprocessors, communications and network processors, etc.), system memory, peripheral devices, and any other hardware components within a system. For example, communications fabric 602 can be implemented with one or more buses.

Memory 606 and persistent storage 608 are computer-readable storage media. In this embodiment, memory 606 includes random access memory (RAM) 616 and cache memory 618. In general, memory 606 can include any suitable volatile or non-volatile computer-readable storage media.

Surface contamination detection program 112 in server 110 is stored in persistent storage 608 for execution by one or more of the respective computer processors 604 via one or more memories of memory 606. In this embodiment, persistent storage 608 includes a magnetic hard disk drive. Alternatively, or in addition to a magnetic hard disk drive, persistent storage 608 can include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 608 may also be removable. For example, a removable hard drive may be used for persistent storage 608. Other examples include optical and magnetic disks, thumb drives, and smart cards that are inserted into a drive for transfer onto another computer-readable storage medium that is also part of persistent storage 608.

Communications unit 612, in these examples, provides for communications with other data processing systems or devices. In these examples, communications unit 612 includes one or more network interface cards. Communications unit 612 may provide communications through the use of either or both physical and wireless communications links. Surface contamination detection program 112 in server 110 may be downloaded to persistent storage 608 through communications unit 612.

I/O interface(s) 614 allows for input and output of data with other devices that may be connected to server 110, camera 122, laser scanner 124, and detector 126. For example, I/O interface 614 may provide a connection to external devices 620 such as a keyboard, keypad, a touch screen, and/or some other suitable input device. External devices 620 can also include portable computer-readable storage media such as, for example, thumb drives, portable optical or magnetic disks, and memory cards. Software and data used to practice embodiments of the present invention, e.g., surface contamination detection program 112 in server 110, can be stored on such portable computer-readable storage media and can be loaded onto persistent storage 608 via I/O interface(s) 614. I/O interface(s) 614 can also connect to a display 622.

Display 622 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method for determining a surface contamination level for a first surface, comprising the steps of:
    a computer receiving a first set of spectral information for a first surface, wherein the first set of spectral information includes a pixel count for each color value of a range of color values, with regard to each color, measured at time one;
    the computer determining whether dispersion of the pixel count across the range of color values, with regard to each color, exceeds a first threshold value;
    the computer determining a surface contamination level based on at least whether the dispersion of the pixel count across the range of color values, with regard to each color, exceeds the first threshold value
    the computer receiving a second set of spectral information for the first surface, wherein the second set of spectral information includes a pixel count for each color value of a range of color values, with regard to each color, measured at time two; and
    the computer determining, with regard to the second set, whether the dispersion of the pixel count across the range of color values, with regard to each color, exceeds the first threshold value.

2. The method of claim 1, wherein the dispersion of the pixel count across the range of color values is equivalent to the standard deviation of the pixel count across the range of color values.

3. The method of claim 1, further comprising the steps of:
    the computer determining that the dispersion of the pixel count across the range of color values, for at least one color, exceeds the first threshold value; and
    the computer determining an amount of cleaning resources to be deployed based on the determined surface contamination level.

4. The method of claim 1, further comprising the steps of:
    the computer determining that the dispersion of the pixel count across the range of color values, for at least one color, does not exceed the first threshold value;
    for color values less than a first peak value, as the color value increases, the computer determining that an amount that the pixel count decreases, exceeds a second threshold value, or, for color values greater than the first peak value, as the color value increases, the computer determining that an amount that the pixel count increases, exceeds the second threshold value, or both, wherein the first peak value is the color value that corresponds to the highest pixel count;
the computer determining a surface contamination level based on the dispersion of the pixel count across the range of color values, for at least one color, not exceeding the first threshold value, and the amount the pixel count decreases, for color values greater than the first peak value, or the amount that the pixel count increases, for color values less than the first peak value, or both, exceeding the second threshold value; and
the computer determining an amount of cleaning resources to be deployed based on the determined surface contamination level.

5. The method of claim 1, further comprising the steps of:
the computer determining that the dispersion of the pixel count across the range of color values, for at least one color, does not exceed the first threshold value;
for color values less than a first peak value, as the color value increases, the computer determining that an amount that the pixel count decreases, does not exceed a second threshold value, and, for color values greater than the first peak value, as the color value increases, the computer determining that an amount that the pixel count increases, does not exceed the second threshold value, wherein the first peak value is the color value that corresponds to the highest pixel count; and
the computer determining a minimum amount of cleaning resources are to be deployed.

6. The method of claim 1, further comprising the steps of:
the computer determining, with regard to the second set, that the dispersion of the pixel count across the range of color values, for at least one color, exceeds the first threshold value; and
the computer increasing the amount of cleaning resources to be deployed in the future for the determined surface contamination level.

7. The method of claim 1, further comprising the steps of:
the computer determining, with regard to the second set, that the dispersion of the pixel count across the range of color values, for at least one color, does not exceed the first threshold value;
with regard to the second set, for color values less than a second peak value, as the color value increases, the computer determining that an amount that the pixel count decreases, exceeds a second threshold value, or, for color values greater than the second peak value, as the color value increases, the computer determining that an amount that the pixel count increases, exceeds the second threshold value, wherein the second peak value is the color value that corresponds to the highest pixel count; and
the computer increasing the amount of cleaning resources to be deployed in the future for the determined surface contamination level.

8. The method of claim 1, further comprising the steps of:
the computer determining, with regard to the second set, that the dispersion of the pixel count across the range of color values, for at least one color, does not exceed the first threshold value;
with regard to the second set, for color values less than a second peak value, as the color value increases, the computer determining that an amount that the pixel count decreases, does not exceed a second threshold value, and, for color values greater than the second peak value, as the color value increases, the computer determining that an amount that the pixel count increases, does not exceed the second threshold value, wherein the second peak value is the color value that corresponds to the highest pixel count; and
the computer decreasing the amount of cleaning resources to be deployed in the future for the determined surface contamination level.

9. A computer program product for determining a surface contamination level for a first surface, the computer program product comprising:
one or more non-transitory computer-readable storage devices and program instructions stored on at least one of the one or more non-transitory computer-readable storage devices, the program instructions comprising:
program instructions to receive a first set of spectral information for a first surface, wherein the first set of spectral information includes a pixel count for each color value of a range of color values, with regard to each color, measured at time one;
program instructions to determine whether dispersion of the pixel count across the range of color values, with regard to each color, exceeds a first threshold value;
program instructions to determine a surface contamination level based on at least whether the dispersion of the pixel count across the range of color values, with regard to each color, exceeds the first threshold value
program instructions to receive a second set of spectral information for the first surface, wherein the second set of spectral information includes a pixel count for each color value of a range of color values, with regard to each color, measured at time two; and
program instructions to determine, with regard to the second set, whether the dispersion of the pixel count across the range of color values, with regard to each color, exceeds the first threshold value.

10. The computer program product of claim 9, further comprising:
program instructions to determine that the dispersion of the pixel count across the range of color values, for at least one color, exceeds the first threshold value; and
program instructions to determine an amount of cleaning resources to deploy based on the determined surface contamination level.

11. The computer program product of claim 9, further comprising:
program instructions to determine that the dispersion of the pixel count across the range of color values, for at least one color, does not exceed the first threshold value;
for color values less than a first peak value, as the color value increases, program instructions to determine that an amount that the pixel count decreases, exceeds a second threshold value, or, for color values greater than the first peak value, as the color value increases, the computer determining that an amount that the pixel count increases, exceeds the second threshold value, or both, wherein the first peak value is the color value that corresponds to the highest pixel count;
program instructions to determine a surface contamination level based on the dispersion of the pixel count across the range of color values, for at least one color, not exceeding the first threshold value, and the amount the pixel count decreases, for color values greater than the first peak value, or the amount that the pixel count increases, for color values less than the first peak value, or both, exceeding the second threshold value; and
program instructions to determine an amount of cleaning resources to deploy based on the determined surface contamination level.

12. The computer program product of claim 9, further comprising:
program instructions to determine that the dispersion of the pixel count across the range of color values, for at least one color, does not exceed the first threshold value;
for color values less than a first peak value, as the color value increases, program instructions to determine that an amount that the pixel count decreases, does not exceed a second threshold value, and, for color values greater than the first peak value, as the color value increases, the computer determining that an amount that the pixel count increases, does not exceed the second threshold value, wherein the first peak value is the color value that corresponds to the highest pixel count; and
program instructions to determine a minimum amount of cleaning resources are to be deployed.

13. The computer program product of claim 9, further comprising:
program instructions to determine, with regard to the second set, that the dispersion of the pixel count across the range of color values, for at least one color, exceeds the first threshold value; and
program instructions to increase the amount of cleaning resources to be deployed in the future for the determined surface contamination level.

14. The computer program product of claim 9, further comprising:
program instructions to determine, with regard to the second set, that the dispersion of the pixel count across the range of color values, for at least one color, does not exceed the first threshold value; and
program instructions to decrease the amount of cleaning resources to be deployed in the future for the determined surface contamination level.

15. A computer system for determining a surface contamination level for a first surface, the computer system comprising:
one or more processors, one or more computer-readable memories, one or more computer-readable tangible storage devices, and program instructions stored on at least one of the one or more storage devices for execution by at least one of the one or more processors via at least one of the one or more memories, the program instructions comprising:
program instructions to receive a first set of spectral information for a first surface, wherein the first set of spectral information includes a pixel count for each color value of a range of color values, with regard to each color, measured at time one;
program instructions to determine whether dispersion of the pixel count across the range of color values, with regard to each color, exceeds a first threshold value;
program instructions to determine a surface contamination level based on at least whether the dispersion of the pixel count across the range of color values, with regard to each color, exceeds the first threshold value
program instructions to receive a second set of spectral information for the first surface, wherein the second set of spectral information includes a pixel count for each color value of a range of color values, with regard to each color, measured at time two; and
program instructions to determine, with regard to the second set, whether the dispersion of the pixel count across the range of color values, with regard to each color, exceeds the first threshold value.

16. The computer system of claim 15, further comprising:
program instructions to determine that the dispersion of the pixel count across the range of color values, for at least one color, exceeds the first threshold value; and
program instructions to determine an amount of cleaning resources to deploy based on the determined surface contamination level.

17. The computer system of claim 15, further comprising:
program instructions to determine that the dispersion of the pixel count across the range of color values, for at least one color, does not exceed the first threshold value;
for color values less than a first peak value, as the color value increases, program instructions to determine that an amount that the pixel count decreases, exceeds a second threshold value, or, for color values greater than the first peak value, as the color value increases, the computer determining that an amount that the pixel count increases, exceeds the second threshold value, or both, wherein the first peak value is the color value that corresponds to the highest pixel count;
program instructions to determine a surface contamination level based on the dispersion of the pixel count across the range of color values, for at least one color, not exceeding the first threshold value, and the amount the pixel count decreases, for color values greater than the first peak value, or the amount that the pixel count increases, for color values less than the first peak value, or both, exceeding the second threshold value; and
program instructions to determine an amount of cleaning resources to deploy based on the determined surface contamination level.

18. The computer system of claim 15, further comprising:
program instructions to determine that the dispersion of the pixel count across the range of color values, for at least one color, does not exceed the first threshold value;
for color values less than a first peak value, as the color value increases, program instructions to determine that an amount that the pixel count decreases, does not exceed a second threshold value, and, for color values greater than the first peak value, as the color value increases, the computer determining that an amount that the pixel count increases, does not exceed the second threshold value, wherein the first peak value is the color value that corresponds to the highest pixel count; and
program instructions to determine a minimum amount of cleaning resources are to be deployed.

* * * * *